United States Patent [19]

Avrameas et al.

[11] Patent Number: 4,970,156

[45] Date of Patent: Nov. 13, 1990

[54] IMMOBILIZATION OF ACTIVE PROTEIN BY CROSS-LINKING TO INACTIVE PROTEIN

[75] Inventors: Statis Avrameas, La Celle Saint Cloud; Georges Broun, Rouen; Eric Selegny, Rouen; Daniel Thomas, Rouen, all of France

[73] Assignee: Agence Nationale de Valorisation de la Recherche, France

[21] Appl. No.: 775,956

[22] Filed: Sep. 13, 1985

Related U.S. Application Data

[63] Continuation of Ser. No. 614,011, May 25, 1984, abandoned, which is a continuation of Ser. No. 369,253, Apr. 16, 1982, Pat. No. 4,464,468, which is a continuation of Ser. No. 254,106, Apr. 14, 1981, abandoned, which is a continuation of Ser. No. 81,255, Oct. 2, 1979, abandoned, which is a continuation-in-part of Ser. No. 922,724, Jul. 7, 1978, abandoned, which is a continuation of Ser. No. 682,255, May 3, 1976, abandoned, which is a continuation of Ser. No. 541,257, Jan. 15, 1975, Pat. No. 4,004,979, which is a continuation of Ser. No. 286,233, Sep. 5, 1972, abandoned, which is a continuation-in-part of Ser. No. 810,835, Mar. 26, 1969, abandoned.

[30] Foreign Application Priority Data

| Mar. 29, 1968 [FR] | France | 68 146205 |
| Jan. 24, 1969 [FR] | France | 69 01451 |
| Mar. 13, 1979 [FR] | France | 69 07897 |

[51] Int. Cl.$^5$ ............ C12N 11/00; C12N 11/02; G01N 33/543; G01N 33/544
[52] U.S. Cl. ............ 435/174; 435/176; 435/177; 435/178; 435/179; 435/180; 436/518; 436/519; 436/524; 436/528; 436/529; 436/530; 436/531; 530/810; 530/811; 530/812; 530/814; 530/815
[58] Field of Search ............ 435/174, 176, 177, 178, 435/179, 181, 182; 260/112 R, 121; 530/810, 811, 812, 813, 814, 815; 436/518, 519, 524, 528, 529, 530, 531

[56] References Cited

U.S. PATENT DOCUMENTS

| 3,639,558 | 2/1972 | Csizmas et al. | 435/181 X |
| 4,004,979 | 1/1977 | Aurameas et al. | 435/181 X |
| 4,464,468 | 8/1984 | Aurameas et al. | 435/177 |

OTHER PUBLICATIONS

Sabatini, et al., The Journal of Cell Biology, vol. 17, 1963 (pp. 19–58).
Schick et al., The Journal of Biological Chemistry, vol. 236, 1961 (pp. 2477–2485).
Silman, et al., Biopolymers, vol. 4, 1966 (pp. 441–448).
Aurameas, et al., Journal of Biological Chemistry, vol. 242, No. 7, 1967 (pp. 1651–1659).
Habeeb, A. F. S. A., Archives of Biochemistry and Biophysics, vol. 119, 1967 (pp. 264–268).
Quiocho, et al., Proc., Natl. Accd. Sci., U.S., vol. 52, 1964 (pp. 833–839).
Clinca Chimica Acta, Romette, 19, 249–253, (1979).
Hackh's Chemical Dictionary, 4th Edition, page 293, McGraw-Hill Book Company, 1969.

Primary Examiner—David M. Naff
Attorney, Agent, or Firm—Berman, Aisenberg & Platt

[57] ABSTRACT

A solution of an active protein substance and an inactive protein substance is reacted with a cross-linking agent, optionally in the presence of an inert carrier, under cross-linking conditions to produce articles comprising both active and inactive protein substances. The active protein substance comprises up to about 20 percent, e.g. from 1 to 20 percent by weight, based on the final weight of the total protein substance, whereas the cross-linking agent comprises from 0.5 to 8 percent by weight, based on the weight of the total treated mixture. The obtained articles are in the form of a solution or a suspension in aqueous medium, in the form of a film, in the form of a membrane, in the form of a fabric, in the form of a porous material, or in the form of a mass, such as granules, pills or tablets.

35 Claims, 4 Drawing Sheets

IMMOBILIZATION OF ACTIVE PROTEIN BY CROSS-LINKING TO INACTIVE PROTEIN

CROSS-REFERENCE TO RELATED APPLICATIONS

The present application is a continuation of Application Ser. No. 614,011, filed May 25, 1984 now abandoned, which is a continuation of Application Ser. No. 369,253; filed Apr. 16, 1982, now U.S. Pat. No. 4,464,468; which is a continuation of Application Ser. No. 254,106, filed apr. 14, 1981, now abandoned, which is a continuation of Application Ser. No. 081,255, filed Oct. 2, 1979, now abandoned, which is a continuation-in-part of Application Ser. No. 922,724, filed July 7, 1978, now abandoned, which is a continuation of Application Ser. No. 628,255; filed May 3, 1979, now abandoned, which is a continuation of Application Ser. No. 541,257, filed Jan. 15, 1975, now U.S. Pat. No. 4,004,979, which is a continuation of Application Ser. No. 286,233, filed Sept. 5, 1972, now abandoned, which is a continuation-in-part of Application Ser. No. 810,835, filed Mar. 26, 1969, now abandoned.

TECHNICAL FIELD

This invention relates to articles containing active protein substances and to the preparation thereof.

More particularly, it relates to a new process of cross-linking active protein together with at least one inactive protein, with or without a pre-existing support or carrier.

Among the active proteins the more interesting ones are enzymes.

BACKGROUND

Enzymes have previously been combined with insoluble supports by using adsorption techniques [I. Langmuir and V. J. Schaefer, *J. Am. Chem. Soc.*, 60, 1351 (1938)], but the products obtained suffered partial denaturation and the enzymes were progressively freed when they were in contact with substrates. Enzyme attachment was therefore not stable or showed poor resistance to external action.

Cellulose derivatives and enzymes have been combined by M. A. Mitz and L. J. Sumonaria [*Nature*, 189, 576 (1969)], who, for instance, obtained a carboxymethylcellulose azide from carboxymethylcellulose and then reacted this azide with a stabilized solution of an enzyme.

Stratis Avrameas (*The Journal of Biological Chemistry*, vol. 242, No. 7, pp 1651 to 1659, Apr. 10, 1967) reported copolymerization of human IgG and rabbit serum albumin at a pH between 4.5 and 5 with ethyl chloroformate to form a gel. As ethyl chloroformate was insoluble in the medium employed, the use of a non-aqueous solvent was necessary and the gel was that formed at the interface between two phases. Such gel could not in any way be formed into a self-supporting sheet or membrane; it is a polymeric precipitate with inadequate mechanical (strength) properties for such purpose.

A process is described in J. Epstein and B. Anfinsen's article, *J. Biol. Chem.*, 237 (1962), dealing with coupling carboxymethylcellulose with ribonuclease or trypsin.

P. Bernfeld et al's article, *Science*, 142, 678 (1963), described a process for making antigens and enzymes insoluble by entrapping them in latticcs of synthetic polymer. The process consists of mechanically entrapping soluble macromolecular products in the lattice of a highly crosslinked Polymeric material by polymerizing some synthetic monomers in an aqueous solution in the presence of the biologically-active macromolecular substance to be embedded.

Goldman et al. (*Biochemistry*, vol. 7, No. 2, Feb. 1968, pages 486 to 500) disclose that active Papain-Collodion membranes may be formed by using bisdiazobenzidine-2,2'-disulfonic acid as cross-linking agent, but it could easily be shown that various other crosslinking agents will not give rise to an active papaincontaining membrane. Therefore, Goldman et al's disclosure is limited to the use of a specific carrier, a specific cross-linking agent and a specific enzyme. Moreover, Goldman et al clearly teach that bisdiazobenzidine derivatives inactivate the protein to a large extent since too much of it is required to insolubilize the protein.

Hornby et al [*Biochem. J.*, Vol. 98, pages 420 to 424 (1966)] describe the preparation of ficin chemically attached to CM-celluloses using a method described by Mitz and Summaria; they describe neither the use of cross-linking agents nor their effect on the activity of the protein-active substance.

Moreover, several authors described the preparation of water-insoluble derivatives of enzymes:

(1) by chemical attachment of the enzyme to a reactive polymer Bar-Eli, A. & Katchalski, E., *Nature*, Lond., 188, 856 (1960) and *J. Biol. Che.*, 238, 1690 (1963); U.S. Pat. No. 3,574,062; Cebra, J. J., et al, *J. Biol. Chem.*, 236, 1720 (1961); Levin, Y., et al, *Biochemistry*, 3, 1905 (1964); Mitz, M.A.m & Summaria, L. J., *Nature*, Lond., 189, 576 (1961); Manecke, G., *Pure appl. Chem.*, 4, 507 (1962); Habeeb, A.F.S.A., *Archives of Biochemistry and Biophysics*, 119, pages 264 to 268 (1967)];

(2) by physical adsorption of the enzyme to a charged polymer [Mitz, M.A., *Science*, 123, 1076 (1946); Mc Laren, A.D., & Estermann. E. F., *Arch. Biochem. Biophys.*, 61. 158 (1956); Barnett, L., & Bull, H., *Biochem. biophys. Acta*, 36, 244 (1959); and Nikolaev, A. Y., & Mardashev, S.R., *Biokhimiya*, 26, 641 (1961); and Nikolaev, A. Y., *Biokhimiya*, 27, 843 (1962);

(3) by entrapping the enzyme in the insoluble matrix of a cross-linked polymer [Bernfield, P., & Wan, J., *Scioence*, 142, (1963)]; and (4) by cross-linking of an enzyme by a bifunctional reagent Habeeb, cited above; and Quische, F. A., & Richards, F. M., *Proc. Nat. Acad. Sci.*, 52, 833 (1964)], the latter consisting of linking molecules of a pure crystallized enzyme carboxypeptidase, the enzymatic activity being thereby greatly reduced.

These previously known processes have several drawbacks, including, interalia:

yields of immobilized active protein are low and, especially when a carrier iith covalent bonding is used, they are strictly dependent on the reactive sites present thereon, the active protein is not securely attached, and the active protein is denatured during attachment.

SUMMARY OF THE INVENTION

The invention has two major inseparable aspects. One concerns novel immobilized active protein, and the other concerns processes for producing the novel immcbilized active protein.

The product, i.e. the immobilized protein, comprises compounds wherein active protein is chemically bound to inactive protein through bridges provided by a bi- or poly-functional cross-linking agent. Although no carrier is required to produce the immobilized active protein in the form of a self-sustaining flexible sheet or film, the inactive protein is optionally employed in a suitable form to serve this purpose. Alternatively, a separate, inert, non-proteinic carrier is used to impart form and additional strength to the product. An open-cell foam or sponge form of the product is also contemplated.

Although the active protein is preferably an enzyme, its scope is virtually unrestricted. It includes antigens, allergens, antibodies, hormones and proteinic parts of viruses or of cells. It also includes, e.g., pepsin, ilisin, trypsin, chymotrypsin and papain, as well as active protein found in microbes. Illustrative of the enzymes are: glucose-oxidase, carbonic anhydrase, proteolytic hydrolase, lypolytic hydrolase, amylolytic hydrolase, urease, asparaginase, uricase, peroxidase, catalase, phenylalanine-hydroxylase, galactose phosphate uridyl transferase, pronase, collagenase, keratinase, elastase, urate oxidase, tyrosine decarboxylase, hexokinase, phosphatase, L-amino-acid-oxidase, xanthine oxidase, decarboxylase, ribonuclease, o-amylase and $\beta$-galactosidase.

The inactive protein is, e.g., albumin, plasma protein, ovalbumin, fibrinogen, gelatin or hemoglobin, as well as inactive protein found in microbes.

Although other cross-linking agents are useful to produce one of the contemplated solid products, glutaraldehyde is the only cross-linking agent presently known to be effective for producing both self-supporting membranes or sheets and porous (freeze-dried) immobilized protein substances. Porous particles are obtained through a cross-linking process at sub-zero (degrees centigrade) temperatures.

Examples of non-proteinic carriers are cellulose, regenerated cellulose, amylose, alginates, polysilanes, dextran, polyvinyl alcohol, cellophane, aminated paper, polyacrylamides, silicone sheet, activated carbon and silk. This list is merely illustrative, and artisans will readily appreciate from it the diverse types of carrier that are contemplated.

The process comprises dispersing, mixing and reacting:

(a) active protein and
(b) inactive protein simultaneously with
(c) cross-linking agent in solvent-containing reaction medium (in which at least the active protein and cross-linking agent are dissolved) under cross-linking conditions (including a pH in the range of from about 5 to about 8 which is conveniently controlled by a suitable buffer) until immobilized active-protein substance is formed. The reaction medium is advantageously spread out during cross-linking so that the volume of solvent is reduced by evaporation (for obtaining membranes) or fractional crystallization (for obtaining porous particles) during this procedure. ln th ⒭immobilized active-protein substance the active protein is chemically bound to the inactive protein by bridges provided by the cross-linking agent which reacts with reactive functions of the active protein and reactive functions of the inactive protein. The active protein comprises up to about 20 percent by weight of the total (active plus inactive) protein in the immobilized active-protein substance, whereas the crosslinking agent comprises from about 0.1 (preferably from about 0.5) to about 8 Percent by weight, based on the total weight of the solventcontaining reaction medium [including (a), (b) and (c)].

The inactive protein is advantageously also in solution during the cross-linking reaction, but such need not be the case. The inactive protein is optionally, e.g., in the form of carrier to which the active protein is chemically bound. Alternatively, the entire reaction is effected on or throughout an inert non-proteinic carrier.

An object of this invention is to provide a process which overcomes the aforesaid drawbacks and which leads to products containing active protein substances and wherein a high proportion of the active protein is attached to a base or carrier.

A further object of this invention is to provide a process for producing products containing active protein and in which the attachment of said active protein to a base or carrier is stable.

Another object of this invention is to provide a process for attaching active protein to a carrier and in which the active protein is not denatured during such attachment.

A still further object is to provide a process wherein active protein substance is cross-linked together with inactive protein, using a cross-linking agent with or without a pre-existing inert carrier.

An additional object of this invention is to provide immobilized active protein in the form of a compound in which the active protein is cross-linked and thus chemically bound to inactive protein through bridges provided by a cross-linking agent (especially those produced by using glutaraldehyde under cross-linking conditions), the weight ratio of active protein to inactive protein in the compound being at most 1 to 4 and the proportion of cross-linking-agent-based bridges in the compound being sufficient to provide a solid immobilized active protein substance without saturating all available reactive functions of the active protein.

Other objects are apparent from the following details.

DETAILS

Figure 3:
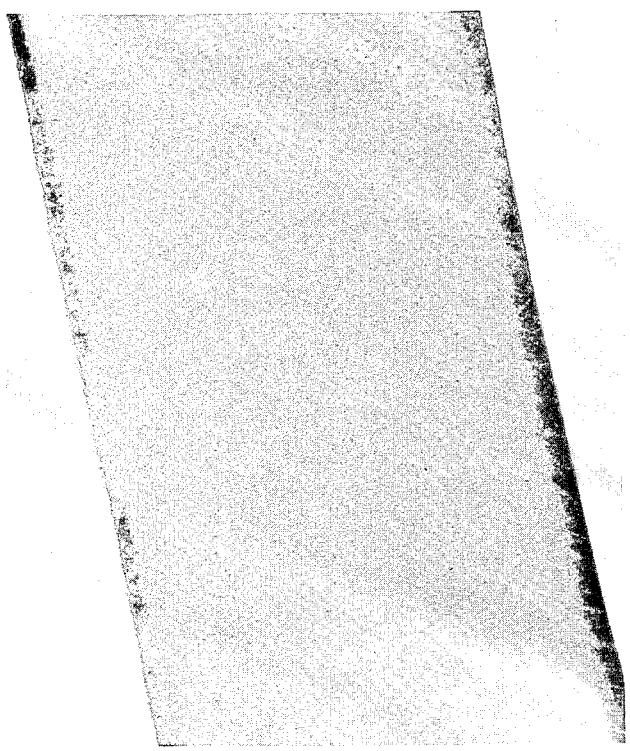
FIGS. 1, 2 and 3 are photographs (at different magnifications) of a self-supporting film or membrane according to this invention.

The process more particularly comprises (a) reacting a solution of an active protein substance and an inactive protein substance with a cross-linking agent, e.g., in the presence of a carrier, under cross-linking conditions (the active protein substance comprising up to about 20 percent, e.g. from 0.5 or 1 to 20 percent and preferably from 1 to 10 ˙peroent, by weight, based on the final weight of total protein substance, and the cross-linking agent comprising from 0.5 to 8 percent by weight, preferably from 1 to 2.5 percent by weight, based on the weight of total treated mixture), (b) removing unattached molecules and, optionally, (c) drying.

According to one particularly advantageous embodiment of the invention, the carrier itself is constituted by inactive protein, more especially by at least one inactive protein which is, optionally, coreticulated together with the biologically-active protein substance.

It has surprisingly been found that cross-linking of biologically-active protein, such as enzymic molecules, together with an inactive protein, such as human or animal plasma albumin or plasma proteins, ovalbumin, fibrinogen or hemoglobin, by means of a cross-linking agent, i.e. a bifunctional or polyfunctional agent, optionally in the presence of a suitable carrier and preferably within the previously-noted range of active protein to total protein substance, needs smaller amounts of cross-linking agent and provides higher activity ratios than previously-known techniques wherein no-such high amount of inactive protein was used. This process is a simple one which is carried out in one step and is performed in a short period of time.

Cross-linking active protein together with at least one inactive protein according to the invention gives rise to better activity ratios than cross-linking in a carrier without inactive protein, this having been verified with all enzymes tested by both methods. The activity remaining in products obtained according to the invention appeared to be a function of the amount of cross-linking agent; too small amounts of cross-linking agent, i.e. less than 0.1 percent by weight, cannot result in insolubilization, and the activity shows a maximum for concentrations lower than 8 percent by weight, a saturation of the active sites appearing at higher rates.

While the present invention is not confined to any particular theory, it is believed that the process according to the invention involves a competition of active and inactive proteins for the cross-linking agent, thus restricting the number of amino groups of each molecule to be involved in the cross-linking step. The active protein molecules are only slightly modified and few active sites are affected by steric hindrance or by denaturation. Their activity is well preserved, for example, in a macromolecular structure where the framework is cross-linked albumin.

Moreover, the process according to this invention ensures a homogeneous distribution of active protein molecules inside the product, thus facilitating the mathematical analysis of such experimental models, for example, of membrane behavior. This process allows the insolubilization of fragile enzymes and scarcely restricts the access of cofactors or coenzymes, Furthermore, cross-linking within a pre-existing carrier, such as a membrane, is particularly suitable for various experimental and technical purposes, since said carrier can be selected in accordance with the needs of each experimental or technical condition. The enzymic-activity yields of the products according to this invention range in most cases between 30 and 80 percent of the activity of the untreated biologically-active protein substance. Thus, even fragile enzyme systems, for instance those using mobile cofactors, are efficiently immobilized. In case of membrane structures, for example, the activity of enzyme bearing products remains unaltered for as long as several months at 4° C.

Many applications of such a process are possible, and consequently numerous applications of it are readily carried out. Alternative procedures are described in greater detail in this specification, where illustrative examples of substrates and actvve protein substance to which the invention is applied are given.

Generally speaking, the active protein substance which is useful in the process of this invention is a natural or synthetic product, and it is used in the crude state or after prior purification. The active protein substance is, e.g., an enzyme, an antibody, an antigen, an allergen, a hormone, a virus or active protein substance found in microbes.

The inactive protein substance which is useful in the process of the present invention is, e.g., human or animal plasma albumin, or plasma protein, ovalbumin, gelatin, fibrinogen or hemoglobin, or any mixture thereof.

Active-protein- and inactive-protein-containing solutions are usually dissolved in aqueous buffer media. The buffers are most frequently inorganic buffers containing, for example, alkaline or alkaline-earth phosphates and are well known to those skilled in the art. Those proteins regarded as active proteins and those which are regarded as inactive proteins are also known to the artisan.

In the process of the invention, any suitable carrier compatible with the active protein substance is useful. The selected carrier is one that is not liable to denature the active protein substance. The product obtained by such process is optionally provided with any of various shapes.

The products include those which are water soluble and which are thus optionally in the form of an aqueous solution. They also include insoluble products suspended in an aqueous medium, as well as solid masses, such as granules, pills, tablets, or a plate, cake or other molded mass. The employed carrier can also provide the article with its final form, such as a film, membrane or an inert porous material. The following cellulose, regenerated cellulose ("Cellophane"), amylose, alginates, dextran, polyvinyl alcohol, polysilanes, polyacrylamide and their substitution products, are illustrative of useful macromolecular carriers. Other examples of suitable carriers or supports are apparent from the following detailed description.

As used herein, the term "alginates" includes salts of a hydrophilic and colloidal hydrocarbon acid, extracted from seaweeds which form their cellular walls (membranes), as a complex of calcium or magnesium.

In this specification the term "cross-linking agent" represents any agent chemically capable of combining with at least two molecules of the chemical compounds with which it is brought together. As a general rule, therefore, said cross-linking agents are bifunctional compounds, but polyfunctional compoonds are also included. Compounds having multiple, identical or different, functions are used as cross-linking agents. These include bis-diazobenzidines, bis-diazo-o-anisidine, biepoxides, chloro-5-triazines, diisocyanates and dialdehydes (e.g. glutaraldehyde, bismaleimides, ethylchlorocarbonates and carbodiimides). Glutaraldehyde is the cross-linking agent of choice; it produces good to excellent results under conditions for which other water-soluble cross-linking agents yield little or no useful product. To obtain the results which characterize this invention, it is essential that both the active protein and employed cross-linking agent (and, preferably, the inactive protein as well) be soluble in a common (ideally aqueous) solvent medium in which cross-linking is effected. This is required to obtain immobilized active protein in the form of integral shaped solid products having useful mechanical (strength) properties.

The process of the invention effects immobilization of molecules of active and/or inactive protein substance, optionally in the presence of a carrier, by the action of a cross-linking agent.

When the carrier is of the macromolecular type and is penetrable by the solution of active and inactive protein substance, molecules of the protein substance are entrapped in the lattice of the carrier. Furthermore, when the carrier possesses functional groups effective to react with the cross-linking agent, direct chemical bonds are set up between the carrier and the protein substances; this further adds to the solidity of the attachment, while in no way modifying the protein substances so attached. Such functional groups are known to those of ordinary skill in the art and are not, per se, the substance of this invention.

In order to obtain a shaped solid product having suitable mechanical strength and other useful physical properries, it is essential that the total cross-linked protein comprise at most 20 percent by weight of active protein and a least 80 percent by weight of inactive protein.

There are at least five distinct solid products that are clearly contemplated by this invention:

1. Active protein (AP) cross-linked to inactive protein (IP) in a ratio of at most 1:4 at a pH, e.g. from 5 to 8, suitable to maintain sufficient reactive functions to yield a solid, shaped product having valuable physical properties. [The "reactive functions" are well known to those skilled in the art; they are functional groups which are part of a particular protein's molecular structure and which are capable of reacting with a cross-linking agent. Reactive functions include, e.g., hydrogen atoms of an amino or carboxylic group, or even (but secondarily) any other free hydrogen atom a proteinic structure may comprise.] A buffer is ordinarily employed in a solvent medium to maintain cross-linking conditions during reaction with a cross-linking agent. An embodiment with a microbe source of both the AP and the IP is of particular interest, especially when the AP and the IP are derived from the same microbe source. [Every microbe is capable of providing a source for both AP and IP.]
2. Product (1) in the form of a self-sustaining flexible sheet or film without the use of a separate or distinct carrier; a variation of this product is one wherein the IP is in carrier or sheet form at the time of crosslinking.
3. Product (1) formed in a sheet or film on an inert non-proteinic carrier, which adds form and strength to the product.
4. Product (1) in the form of open-cell foam or sponge, as necessarily results from the process, e.g., of Example 6.
5. Product (1) formed in a sheet or film throughout a macroporous inert non-proteinic carrier.

The essence of the invention is providing a self-sustaining optionally-shaped solid product having a significantly-higher concentration of immobilized active protein than was previously possible. This is accomplished by cross-linking active protein in a solvent medium with at least four times as much inactive protein, with or without carrier, and while maintaining the pH at a level which favors such cross-linking. Two completely distinct and entirely different immobilizedprotein novel forms are made possible. One of these is a self-sustaining flexible film or sheet having good physical properties (including substantial mechanical strength) and being free from a non-proteinic support or carrier. The other is an open-cell sponge-like solid composed virtually entirely of active protein cross-linked to inactive protein through linkages provided by glutaraldehyde as a cross-linking agent.

Figure 1:
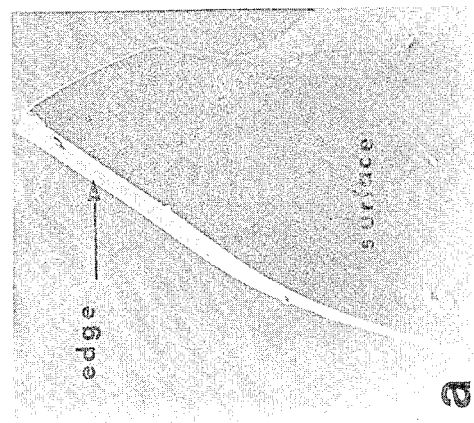

The different solid shaped (carrier-free) products are illustrated in the drawings. FIG. 1 shows a membrane prepared according to this invention from glucose oxidase, glutaraldehyde and bovine albumin and having a thickness of about 50 microns, as observed by sweeping electron microscopy. The view provides an appreciation of the nature and constitution (the actual physical aspect) of the product.

Figure 2:
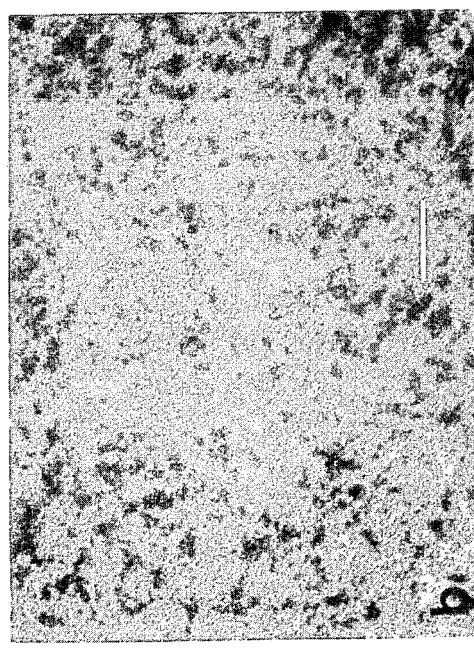

FIG. 2 is a photograph of the surface of the same membrane, as observed by transmission electron microscopy. The bar (bottom right side) corresponds to a length of 1000° Å. The product is shown to have a very regular structure and comprises neither holes nor pores.

FIG. 3 is an outer view of a cut part of the same membrane by transmission electron microscopy at a magnification of 20,000. It confirms that the product is very homogeneous and that both of the outer surfaces are planar and parallel to each other.

Figure 4:
FIGS. 4 to 11 are photographs of open-cell sponge or foam, such as that produced by the procedure of Example 6.
Figure 5:
Figure 6:
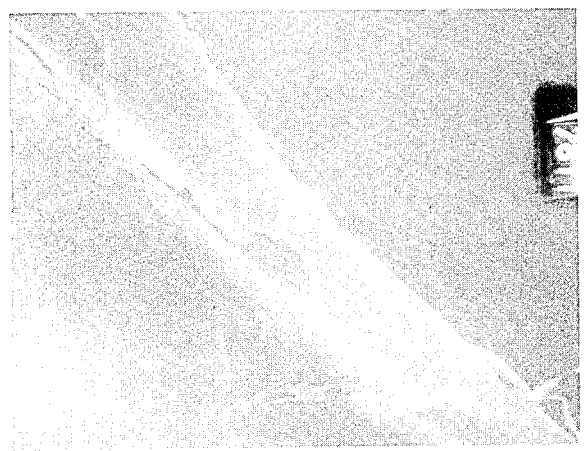
Figure 7:
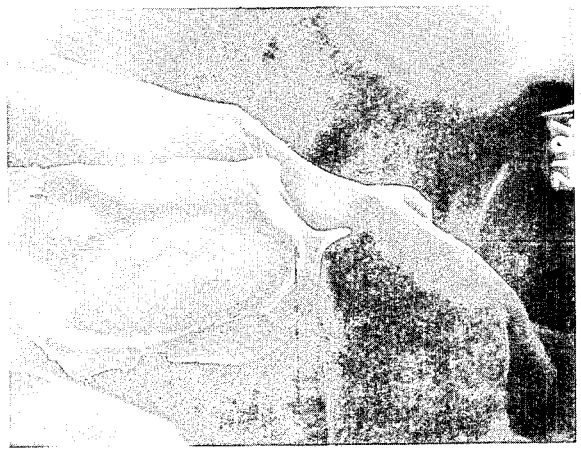
Figure 8:

FIGS. 4 to 11 are photographs (at different magnifications) of the open-cell sponge or foam form observed by scanning electron microscopy. FIGS. 4, 5 and 7 are at 140×, 280× and 280×, respectively. FIG. 6 shows (at 2600X) detail of that section marked A in FIG. 5, and FIG. 8 shows (at 2600×) detail of that section marked B in FIG. 7.

The photographs of FIGS. 4 to 8 were taken after grinding. This is of particular interest since such products are actually used in ground form in industrial reactors. These views show that the product has an internal dense and solid (but porous and with very open cells) structure. Such products are thus appropriate for being packed into reactors; they have the dual advantage of making it possible to prepare highly-packed bed reactors (in view of their high mechanical strength) and permitting an easy flow of liquids to be treated (in view of the structure which appears very porous in nature).

There was no intention to show any special or particular part of the structure by the magnification of details A and B. Said details were not specifically selected as representing the only interesting parts; they were chosen as mere examples of a part of the product which has been observed at higher magnifications to show both the strength and porosity of the product better.

Figure 9:
Figure 10:
Figure 11:

FIGS. 9 and 10 are surface photographs at magnifications of 30X and 50×, respectively. FIG. 11 shows (at 480×) detail of that section marked C in FIG. 10.

FIGS. 9 to 11 are photographs of the same opencell sponge or foam form (observed by scanning electron microscopy) as seen in FIGS. 4 to 8, but without prior grinding; they represent the outer view of the open-cell sponge or foam form of the product of this invention. Here again the product appears very strong and porous, simultaneously; as concerns detail C, the previous comments concerning details A and B similarly apply.

The reaction of active protein and inactive protein with cross-linking agent has two concurrent aspects which combine to yield an insoluble solid product. The relationship between chain growth (polymerization) and forming bridges between reactive sites (cross-linking) determines the ultimate physical structure and properties of the resultant product. As illustrated, e.g., by Example 1, cross-linking and solvent removal are effected simultaneously, i.e. crosslinking continues while solvent is evaporating. Similarly, coreticulating can be effected while reducing the amount of reaction medium solvent in a corresponding process comprising coreticulating and chemically binding dissolved active protein together with dissolved inactive protein in a buffered water-based reaction medium without a preexisting carrier.

Two concurrent intrinsic effects are made possible by this invention. Active protein is immobilized (stabilized against denaturation or degradation) to such an extent by this invention that such protein (otherwise subject to material denaturation or degradation within about one day) can now be stabilized for periods up to a year or even longer. In addition to the fact that immobilized active protein can now be prepared in the form of desired solid shapes having useful physical strength and other advantageous mechanical properties, the concentration of such immobilized active protein is significantly increased (e.g., from 50 to 75 fold) even over that obtained by prior attempts (Habeeb, A.F.S.A., *Archives of Biochemistry and Biophysics,* 119, 264 to 268, 1967) to conjugate active protein (trypsin) to a carrier having reactive sites (aminoethyl-cellulose).

A particular embodiment, whether in the form of a self-supporting film or porous open-cell foam or sponge, is that illustrated by Example 3 wherein both the active and the inactive proteins are provided by the same source. Such a source is, alternatively, whole microbe cells, e.g. submitted to sonication or other lysis.

Porous or open-cell, sponge-like solid products are inherently produced by the general freeze/thaw process illustrated by Example 6, which provides an alternative method of effecting cross-linking while removing solvent.

The open-cell foam or sponge is characterized by the following physical constants:
 Surface area: about $10^3$ cm$^2$/cm$^3$; about 1 m$^2$/g when dry
 Specific gravity: about 0.1 when dry (including open cells)
 Free volume: about 90%
 Open cell sizes ranging from 1 $\mu$ to 200 $\mu$
 Capacity for absorption of water: about 10 times its volume for entire product including open cells, when starting with a dry material
 Capacity of absorption: about 30% when dealing only with insoluble phase
 Elasticity (tension modulus) 0.4 to 0.7 kg/mm$^2$
 Compression: 0.2 to 0.9 kg/mm$^2$

EXAMPLES

The following examples are merely illustrative of and do not in any way limit the claimed invention.

In one application of the process of the invention, an enzyme, such as glucose-oxidase, carbonic anhydrase, chymotrypsin or trypsin, is immobilized through a crosslinking agent, such as bis-diazo-o-dianisidine, onto a substrate consisting, for instance, of cellulose, regenerated cellulose, such as the material commercially available under the name of "Cellophane", dextran or a polyvinyl alcohol, the substrate or carrier being in granular or sheet form.

In another application of the process of the invention an enzyme, such as glucose-oxidase, is attached by copolymerization to an inert protein, such as albumin, acting as a carrier-forming substance, in the presence of a cross-linking agent, such as glutaraldehyde. In the same way, an active protein film is prepared by cross-linking albumin and carbonic anhydrase through a bifunctional reactive compound, for example glutaraldehyde. The film so obtained possesses advantageous properties and is, for instance, useful as a biological membrane. Other enzymes are alternatively incorporated in such a film, bestowing on it the specific properties of the enzyme in question, as in the case of carbonic anhydrase.

In another application of the process of the invention, a film of carbonic anhydrase and an inactive protein substance, such as albumin, cross-linked with a bifunctional reactive compound, e.g. glutaraldehyde, is deposited on the surface of a hydrophobic membrane, and notably a membrane containing silicone. The deposit of this carbonic anhydrase and albumin film on the surface of such a membrane greatly increases the velocity of gas transfer, notably carbon dioxide, through the membrane.

In another application of the process according to the invention, a fabric bearing grafted proteolytic enzyme is manufactured by soaking the initial fabric first in a solution of a hydrolytic enzyme and an inactive protein, then in a solution of a bridging agent, e.g. glutaraldehyde. After rinsing, a fabric is obtained containing enzyme which retains its activity therein.

In another application of the process according to the invention, an active protein, such as an enzyme, an antigen or similar protein substance, is polymerized in the presence of a bridging agent as well as an inert protein acting as a carrier-forming substance, and polymerization is stopped so that the product obtained remains soluble in aqueous solvents.

In this case, the active protein is grafted onto a carrier formed of a water-soluble inactive protein chain.

Glutaraldehyde is particularly useful as a bridging agent.

Plasmatic albumin, for instance, is useful as an inert carrier-forming protein substance.

The following active proteins are optionally cross-linked to inert protein.

Hydrolytic enzymes, such as the proteolytic, lipolytic and amylolytic hydrolases of the digestive tract, as well as urease, asparaginase and other hydrolytic enzymes; oxidases, such as uricase, glucose-oxidase, peroxidase and catalase; hydroxylases, such as phenylalaninehydroxylase; isomerases and transferases, such as galactosephosphate uridyl transferase; and lyases breaking C—C, C—O and C—N bonds.

Active proteins, including soluble antigens and allergens, are also used; as in the case of enzymes, these protein fractions having previously been isolated from their natural insoluble substrate.

The process is useful for preparing therapeuticallyactive products in which the availability of active proteins is improved.

Proteolytic enzymes immobilized in accordance with this process are, e.g., administered orally to facilitate or activate digestion.

The obtained enzyme solutions are administrable by intraveneous injection. Certain enzymes, such as uricase and asparaginase, which have a therapeutic effect on gout and acute leukosis, respectively, are similarly injected in this way.

Galactose-phosphate uridyl transferase, as well as phenylalanine hydroxylase, are administered to subjects who are devoid of the capacity to manufacture certain enzymes or who secrete them in insufficient amounts in order to effect normal metabolism.

The injection of antigens immobilized according to this invention permits the permanent formation of antibodies to be induced over a long period of time; that of allergens enables the receiver's organism to be desensitized in a lasting manner.

In all cases, proteins immobilized according to this invention provide delayed action or prolonged therapeutic effects when they are administered, owing to the constitution of the products obtained by such a process.

In one embodiment of the process according to the invention, the active proteins are polymerized, in the presence of a cross-linking agent, with an inactive protein carrier-forming substance (but without a pre-existing support) to create a small, insoluble pproduct, such as to be suspended in a physiological or aqueous solution.

The preferred inactive carrier-forming protein substance is albumin and the cross-linking agent is, for example, glutaraldehyde. The active protein molecules effective to be immobilized are, e.g., enzymes, antigens, antibodies, allergens, viruses or other protein substances, including those found in microbes. The active protein substance is useful in its crude state or after preliminary purification. According to said process, suspensions containing proteolytic enzymes, lyases breaking C—C, C—O and C—N bonds, oxydoreductases, isomerases, transferases or other enzymes are formed. Furthermore, the process of this invention provides suspensions which are therapeutically useful. Thus, grafted enzymes of a proteolytic, lipolytic or amylolytic nature are administered per os to activate digestion. Suspensions of enzymes, such as uricase or asparaginase, for instance, are administered by subcutaneous, intramuscular or intraveneous injection to degrade certain harmful products, such as uric acid, or to degrade asparagin in some diseases or to make up the chronic insufficiencies found in certain subjects, such as the available amounts of galactose phosphate uridyl transferase found in subjects suffering from galactosemia. Similarly, antigens are injected subcutaneously to initiate the lasting formation of the corresponding antibodies; likewise, the injection of allergens immobilized onto pproducts favor desensitization to these proteins. Furthermore, membranes of bacterial origin or whole bacteria are coupled to albumin molecules to form pproducts capable of initiating the formation of antibacterial antibodies in a very lasting manner; similarly, coupling viruses to inactive proteins, such as albumin, is effected. These couplings enable effective vaccinations, especially local vaccinations, as is the case with rhinopharyngeal vaccination, or the supply of germs competing with disordered intestinal flora.

In another application of the process according to the invention an active protein is polymerized in the presence of a cross-linking agent and an inactive carrier-forming protein until a solid and insoluble mass of sufficient size is obtained, said mass containing active protein which has retained its initial properties. In this case, the active protein is grafted onto a support of an insoluble protein mass in, for instance, the form of granules, pills or tablets. Many enzymes are so incorporated into a plasmatic albumin polymer, particularly proteolytic, lypolytic and amylolytic hydrolases; the same holds true for certain microorganisms, which are linked to albumin molecules by protein in their walls. Such immobilized protein and such immobilized microorganisms are administrable per os either to accelerate digestion or to counteract pathological intestinal flora.

In another application of the process according to the invention, at least one enzyme or any other active protein is polymerized (in the presence of a cross-linking agent) in combination with an inactive protein within an inert material, such as a prosthesis, a product used in plastic surgery, etc., having a slight surface porosity which permits penetration and fixation of said active and inactive proteins. In this case, the active proteins are immobilized in a carrier consisting of a very slightly porous and insoluble inert material.

Such treated prostheses, consisting either of a simple protein film or a film bearing enzymic functions, are useful either to facilitate the covering of prostheses surfaces by neighboring tissues or to prevent such covering. This is particularly the case with prostheses used in plastic surgery, Starr's valve, parts used in osteosynthesis, and all surfaces of insoluble and inert material introduced into the system as a material used in plastic surgery or prostheses The process of the invention further provides products in which the enzymes are immobilized onto a substrate represented by a protein film. After suitable treatment such films are also useful in cosmetology and therapy.

In such cases, the films obtained by enzyme immobilization should be dried and sterilized by ultraviolet rays before being packed in sterile containers.

The cutaneous application of such films or their application to readily-accessible mucous membranes permits local action of certain enzymes, notably proteolytic enzymes, such as trypsin, chymotrypsin, papain, keratinase and elastase, subtilisin, pronase, collagenase, pepsin, etc. These enzymes have a therapeutic effect in certain dermatoses and cicatrization problems.

These enzyme-bearing protein films are also useful in cosmetology for care of the skin.

Apart from the aforesaid applications, the products obtained by the process according to the invention are used for active filtration, selective adsorption, electrophoresis, chromatography and other similar applications.

Thus, in the field of active and selective filtration a solution of proteins is degradable into corresponding amino acids and peptides by filtration through a membrane bearing a proteolytic enzyme, such as trypsin, after treatment according to the process of this invention.

Moreover, in the field of electrophoresis and chromatography, the constants of affinity and transformation of a compound which can be attached by an enzyme is determinable by causing this compound to migrate into an enzymebearing film.

The activity yield after cross-linking according to this invention was measured for various enzymes, such as glucose-oxidase, urease, trypsin, catalase, etc.

Some of the procedures are detailed below, but it is well known to one of ordinary skill in the art how to proceed with other enzymes or other biologically-active protein substances.

(a) Measurement of glucose-oxidase activity

The oxidation of glucose to gluconic acid by glucose-oxidase provides hydrogen peroxide. The reaction becomes irreversible after addition of catalase to the protein-bearing product.

The activity was measured either by observing the disappearance of glucose or by making use of the pH shift occurring during the reaction. In the first case, the remaining glucose was measured in aliquots, using the method of Hyvarinen and Nikila [*Clinica Chimica Acta*, 7, 145 (1962)]. In the second case, the reaction was followed with a pH stat, using a 0.015M glucose solution in 0.005M phosphate buffer. The predetermined pH was maintained constant by the addition of a 0.1M sodium hydroxide solution.

(b) Measurement of urease activity

The hydrolysis of urea into ammonium carbonate was determined either by detecting the appearance of ammonium ions using the well known Berthelot's method therefor or by using a specific cation electrode.

The formation of ammonium carbonate was also determined with a pH stat, using a 0.15M urea solution in a 0.005M phosphate buffer. The predetermined pH was maintained constant by the addition of 0.1M HCl.

(c) Measurement of trypsin activity

Degradation of N-benzoyl-1-arginine ethylester (BAEE) was followed by an increased absorption at 253 nm or by the resulting pH shift. As concerns the spectrophotometric method, a 350 mg/1 solution of BAEE was used in a 0.05M phosphate buffer. Turning now to the pH stat method, the predetermined pH was maintained constant by addition of 0.1M NaOH.

(d) Measurement of catalase ativity

The decrease of hydrogen peroxide, initially present at a rate of 0.01M in a 0.05M phosphate buffer solution, was observed by its absorption at 240 nm.

The activity yields provided by the products obtained by the process according to this invention are measured through an enzymic activity ratio p (where the active protein substances are enzymes), which is defined as:

$$\rho = \frac{\text{activity measured after treatment}}{\text{initial activity in the bulk solution}} \times 100$$

$\rho$ expresses the chemical yield and enzyme activity remaining within the product after the immobilizing treatment according to the invention.

The chemical yield of the immobilization inside the pre-existing carrier or after coreticulation with an inactive protein substance is measured by nitrogen titration (in a C:H:N analyzer).

Thus it appeared that, after cross-linking with an inactive protein according to the process of this invention, all of the active proteinic molecules which were introduced were immcbilized; the chemical yield was consequently exactly 100%, which means that there were no losses in the bath used for the treatment. Moreover, the losses by denaturation are very low, since an enzymic yield of more than 80% may be obtained (on the basis of the activity that has been introduced into the bath).

On the other hand, the process according to this invention is not limited to monoenzyme systems; it also provides sequential enzyme systems or other polyenzymic systems. For example, a structured multilayer bienzymatic membrane (comprising two active protein layers and two selective films, the active enzymatic films carrying, respectively, hexokinase and phosphatase coreticulated with an inert protein, e.g. albumin; both are impregnated with ATP and covered on their external side by two selective films permeable to glucose, but impermeable to glucose-6 phosphate) is prepared by this process.

In this asymmetrical membrane, glucose is temporarily phosphorylated.

The system behaves chemically as a simple ATPase

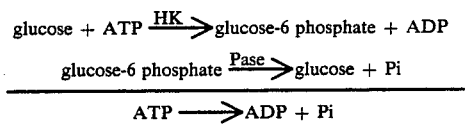

In the first layer glucose is a substrate, and in the second one glucose is a product.

Whichever form they have, the protein-bearing products according to this invention have an increased resistance towards heat denaturation and proteolysis. The active protein substances keep their activity in a buffer at 25° and 37° C. for several months. For instance glucoseoxidase was bound on Cellophane together with albumin according to the invention by means of glutaraldehyde and kept at 37° C. under dry conditions and in solution. One month later the dry product retained all its initial activity, whereas the solution only retained 60 percent thereof. Under the same conditions, free glucose-oxidase lost all its enzymic activity.

The increased resistance to denaturation and proteolysis of enzymes.bound according to this invention was observed with every enzyme tested. Glucose-oxidase, for instance, was submitted to the effect of trypsin, chymotrypsin and an enzymic preparation commercially available under the name "pronase". Glucose-oxidase which was merely solubilized was inactivated in 5 to 20 hours, whereas glucose-oxidase bound by means of glutaraldehyde in a Cellulose membrane together with fibrinogen according to this invention retained 100 percent of its activity after at least as long as 48 hours.

As regards denaturation by heat, two samples were prepared; the first one (1) consisting of glucose-oxidase bound to Cellophane together with albumin, the second one (d) consisting of glucose-oxidase and albumin coreticulated together according to the invention by means of glutaraldehyde, but without any pre-existing carrier. The samples were kept at 55° C. for various periods of time; the enzymic activity was measured at 25° C., which permitted separate consideration of denaturation by heat and by activation energy.

As concerns free enzyme, the activity of free glucose-oxidase decreases down to 50 percent of its initial value in 6 to 7 hours at 55° C. and practically to zero after 40 hours. On the contrary, sample (2) retained more than 90 percent of its activity after 6 to 7 hours at 55° C. and even about 60 percent after more than 40 hours at the same temperature; sample (1) retained about 95 percent of its activity after 6 to 7 hours at 55° C. and about 80 percent of its activity after more than 40 hours at the same temperature.

Thus, while the present invention is not to be confined to any particular theory, it is believed that two phenomena are involved in the stabilization of the active protein within the products containing a high proportion of inactive protein and prepared according to this invention:

insolubilization or gelatinization, which stabilizes the proteinic molecular structure;

local high protein concentration, which has an additional stabilizing effect.

The active proteins immobilized according to this invention are useful in analytical systems other than those specifically described above; still further, the products comprising immobilized active proteins of this invention provide a highly advantageous vehicle for the study of the immobilized active protein itself. Immobilized active protein of this invention is useful for the same purposes and in virtually every way the corresponding active protein is useful in the absence of placing it in the form made possible by the subject invention.

This invention is further illustrated by the following examples:

EXAMPLE 1

Several 0.05 mm thick sheets of "Cellophane" Rhone Poulenc's 550 PTOO were 50/50 impregnated with a solution in water of 2 mg/ml of glucose oxidase and 25 mg/ml of a mixture of albumin and fibrinogen for about 5 minutes. They were then dried by ventilation in a cold chamber. The operation was repeated 1 to 3 times to obtain sheets having different activities. The sheets were then impregnated with a 5 mg/ml solution of bis-diazo-o-dianisidine buffered to pH 6.8 by means of a 0.02M solution containing 3 parts of monobasic sodium phosphate to one part of dibasic sodium phosphate. The glucose-oxidase molecules which had not been immobilized were removed after the sheets had been passed through several agitated rinsing baths. The sheets were then ready to be used as membranes.

The enzymic yield, that is the percentage of the activity introduced within the medium which was retained by the final structure, was found to be 65 percent.

The technique of the preceding example was repeated using carbonic anhydrase, chymotrypsin and trypsin instead of glucose-oxidase; comparable results were obtained.

Such enzymes were also attached to other carriers, such as cellulose, dextran and polyvinyl alcohol, and similar results were obtained.

EXAMPLE 2

25 mg of glucose-oxidase were dissolved in 0.7 ml of phosphate buffer at pH 6.8, and 50 mg of albumin were also dissolved in 0.7 ml of the same buffer. The two solutions were mixed and agitated until a homogeneous mixture was obtained. A solution of 2.5 percent by weight of glutaraldehyde was added thereto drop by drop with agitation. The solution so obtained was placed on a flat-bottomed glass mold having a 40-cm$^2$ surface. After one hour a 0.1 to 0.2 mm thick film was obtained and was kept in water to prevent it from drying out.

The enzymatic yield was found to be 80 percent.

When a carrier impenetrable to protein solutions and solutions of bridging agents was used, a detachable film was obtained that was useful alone or when applied to another carrier.

EXAMPLE 3

3 mg of poorly purified carbonic anhydrase containing about 5 percent of pure enzyme and 95 percent of inactive protein, prepared from ox red blood cells were dissolved in 2 ml of distilled water. To this protein solution 1 ml of a 2.5 percent glutaraldehyde solution in a 0.02 M phosphate buffer (pH 6.8) was added. This mixture was spread on the surface of a hydrophobic silicone membrane commercially available under the name, "Silastic 500-3", and manufactured by Dow Corning and Company: cross-linking was carried out at 4° C. for 12 hours; the solvent was removed by evaporation. A film attached to the membranous carrier was obtained. The excess bridging agent was removed by washing several times in distilled water. The membrane was then rinsed in a 0.022M veronal buffer solution, pH 7.35.

The enzymic yield was found to be about 30 to 40 percent, said yield being not easily appreciated because the methods for enzymic titrations were, in this case, not at all precise.

The depositing of a carbonic anhydrase film on such a membrane multiplied by 2 the velocity of transfer of carbon dioxide between two liquids placed on either side of this membrane. This effect is explained by the acceleration of the conversion $CO_3H^- \rightarrow CO_2 + OH^-$ necessary to pass from the inonized form to the gaseous form of $CO_2$, the only one capable of passing through the "Silastic" membrane, and $CO_2 + OH^- \rightarrow CO_3H^-$ permitting the solubilization and therefore the removal of $CO_2$ from the other side of the membrane.

EXMAPLE 4

A solution of 3 mg of purified carbonic anhydrase was mixed in 0.4 ml of 0.02M phosphate buffer, pH 6.8, with a solution of 50 mg of plasma albumin in 1.4 ml of the same buffer.

1.2 ml of glutaraldehyde at 2.5 percent in solution in distilled water was added to this solution. Cross-linking took place at 4° C. for 12 hours. A continuous, flexible protein film having good mechanical properties was obtained. The molecules which had not reacted were eluated by rinsing with distilled water. The enzymic yield was about 40 percent, the same remark applying as in Example 3.

Such a film, duly rinsed, possesses some of the qualities of biological membranes, notably that of not imparing the figurated elements of blood placed in its contact.

In such a film, other enzymes are alternatively used instead of carbonic anhydrase.

The incorporation of carbonic anhydrase renders this film very permeable to carbon dioxide, permitting its use in oxygenators using membranes.

EXAMPLE 5

Comparative

In 50 ml of 0.05M aoetic acetate buffer pH =5.5, sonicated extracts of *E. coli* (enriched in glycoproteins by selective acid precipitation) were dissolved. The final proteinic concentration was 5 percent in the bulk solution. Ethyl chloroformate was added to a final concentration of 2 percent. The solution was left in a beaker for 10 hours at 20° C. A solid mass precipitated, but its physical (strength) properties were inadequate for it to be used in a reactor.

EXAMPLE 6

In 50 ml of 0.1M phosphate buffer, pH =6.8, containing 8 percent bovine plasmalbumin (w/v), washed *Bacillus subtilis* were suspended to a final concentration of 50 millions of bacterial bodies per milliliter. Cold glutaraldehyde was added to a concentration of 3 percent. The solution was immediately frozen at −60° C. After 2 hours, the suspension was slowly thawed, giving rise to a lamellar structure containing dross-linked extract of the whole bacterial body. The structure was ground and packed in a column. It degraded amylose and dextrins, as confirmed by the increase in reducing power and the decrease of coloration in the presence of iodine.

EXAMPLE 7

A suspension of washed *Penicillium notatum* (10 mg per ml of final mixture) in water was admixed with 2 percent gelatin. To the thoroughly-stirred mixture one volume of 0.1 g/ml of 2,2'-disulfonic bis-diazobenzidine was added slowly and with stirring for each ten volumes of the suspension. The resulting mixture was reacted for 1 hour at 20° C., then spread on a filter paper aerated with a vane. The solid obtained by preventilation was then cut and suspended in a 0.05M phosphate buffer, pH=7.

The resulting flakes metabolize glucose and enable the use of the immobilized microorganisms in continuous flow reactors which can be used for fermentation, therapeutic, and food industries.

EXAMPLE 8

House dust collected and ground was suspended to a concentration of one million pproducts per ml of 0.02M phosphate buffer, pH=6.5, containing 10 mg per ml of human albumin. The mixture was treated with glutaraldehyde at a final concentration of 3 percent at 15° C. for 24 hours. The obtained cake was ground and sterilized with ethylene oxide. The same procedure is used with suspended viruses with substantially similar results.

This procedure allows the realization of allergens which are used by allergologists. The stabilization obtained favors the preparation of injectable suspensions of cross-linked biological pproducts controlled in size and stable for a long time.

EXAMPLE 9

A solution was made containing 150 mg/ml of a protein mixture containing proteolytic and amylolytic enzymes and several inactive proteins and available on the market under the name "Rapidase". 300 ml of this solution impregnate 1 m$^2$ of fabric; the solvent was allowed to evaporate completely at laboratory temperature.

The fabric was then imbibed with 300 ml of a glutaraldehyde solution at 2.5 percent; cross-linking was preferably effected for from 1 to 10 hours; the fabric was then well rinsed in distilled water. The enzymic yield was found to be 75 percent, the basis therefor being the degradation of a carbohydrate substrate having small molecular dimensions (dextrins).

The enzymes introduced into the fabric retained their activity and were notably able to degrade natural substances soaking into the fabric. Soils of blood, sweat and egg were then removed from the fabric simply by rinsing them in water. This action can be explained, without this explanation implying a limitation, by a limited degradation of natural molecules in direct contact with the enzyme-impregnated fabric. The residue of the natural material no longer adheres to the fabric and breaks away in a simple flow of water.

EXAMPLE 10

A solution of 10 mg of glucose-oxidase dissolved in 0.4 ml of 0.02M phosphate buffer, pH 6.8, was mixed with a solution containing 50 mg plasma albumin in 1.4 ml of the same buffer. 1.2 ml of a 2.5 percent solution of glutaraldehyde in distilled water was added to this solution. Cross-linking occurred after one hour at laboratory temperature; 0.05 ml of 0.05M tris-(hydroxymethyl)aminomethane-HCl buffer, pH 7.8, was then added to the reaction mixture, this having the effect of stopping polymerization just before the appearance of an insoluble phase. Albumin chains to which two or more molecules of glucose-oxidase attached were thus obtained. The glucose-oxidase retained its activity and specificity. The products were polymers, as was shown by the measurement of their molecular mass.

The small molecules, such as unreacted glutaraldehyde molecules, were removed by dialysis against 10 volumes of buffer solution, then 10 volumes of water. Each contradialysis liquid was changed hourly, three times over.

The polymer was then freeze-dried; the product was then sterilized with ultra-violet rays and added to an injectable physiological solution; the polymer was very stable under increase in temperature and was resistant to most proteolytic enzymes. The enzymic yield was found to be 60 percent.

Equivalent results were obtained by replacing the glucose-oxidase of the example given above by any enzyme selected from proteolytic, lipolytic and amylolytic hydrolases of the digestive tract, as well as urease, asparaginase and other hydrolytic enzymes; oxidases, such as uricase, peroxidase and catalase; hydroxylases, such as phenylalaninehydroxylase; isomerases and transferases such as galactosephosphate uridyl transferase; lyases breaking C—C, C—O and C—N bonds, and a soluble antigen or allergen previously freed from its natural insoluble support.

EXAMPLE 11

A solution of 15 mg of α-amylase in 0.4 ml of 0.02M phosphate buffer, pH 6.8, was mixed with a solution of 70 mg of plasma albumin dissolved in 1.4 ml of the same buffer.

1.2 ml of a solution of glutaraldehyde at 2.5 percent in distilled water was added to this solution; cross-linking took place for three hours at laboratory temperature; it was stirred slowly. When an insoluble phase appeared, the degree of insolubilization was measured by nephelometry. When the phenomenon had reached the desired level, 0.5 ml of 0.05M buffer tris-(hydroxymethyl)aminomethane HCl, pH 7.8, was added; this stopped the polymerization. A suspension of polymerized inactive pproducts formed of albumin, onto which α-amylase molecules were attached, was obtained; the α-amylase molecules retained their activity and specificity. The enzymic yield was found to be 30 percent, using maltodextrins as a substrate.

Equivalent results were obtained by replacing the α-amylase used in this example with an enzyme selected from proteolytic enzymes, oxido-reductases, lyases breaking C—C, C—O and C—N bonds, isomerases, transferases or other enzymes, and also with an antigen or an allergen.

The fixed active molecules, such as enzymes, antigens and allergens, remained stable by raising the temperature to 50° C. and resisted the attack of proteolytic enzymes.

These pproducts were recovered by filtration on fritted glass, then washed well with the buffer, then with distilled water, until the washing water no longer absorbed light at 280 millimicrons. These pproducts were then dried, pulverized and sterilized by ultraviolet rays. The powder could then be added to an injectable physiological solution.

EXAMPLE 12

A solution of 11 mg of trypsin in 0.4 ml of 0.02M phosphate buffer, pH 6.8, was mixed with a solution of 50 mg of ovalbumin in 1.4 ml of the same buffer.

1.2 ml of a 2.5 percent solution of glutaraldehyde in distilled water was added to this solution. This mixture was placed in molds of the desired shape; cross-linking occurred for 48 hours at laboratory temperature until the material in the mold had completely set. The pproducts so obtained were removed from the mold and then abundantly rinsed to elute unreacted molecules. The efficiency of the rinsing was checked by light absorption at 280 millimicrons; rinsing was considered satisfactory when this absorption was nil. The active molecules attached in this mass retained their activity and specificity. The enzymic yield was found to be 70 percent, using N-benzoyl-1-arginine ethyl ester.

Equivalent results were obtained by sequentially replacing the trypsin in this example by each of the following types of enzymes: a proteolytic, a lipolytic and an amylolytic hydrolase.

EXAMPLE 13

The surface of a product available on the market under the name of "Cellophane" was used as an inert, insoluble carrier; the surface thereof was impregnated with a solution consisting of a mixture of α-chymotrypsin and inert proteins (comprising 20 mg of α-chymotrypsin and 80 mg of inert proteins per ml of 0.02M phosphate buffer at pH 6.8). The carrier was then sprayed twice with a 2.5 percent solution of glutaraldehyde in distilled water. Cross-linking took place after 48 hours at laboratory temperature. The product was then washed well, first with the buffer and then with distilled water to remove molecules which had not reacted or were easily detached from the carrier.

The porous surface of the "Cellophane" sheet was thus covered with a thin film of polymerized α-chyrotrypsin. The active protein molecules, bridged to one another or to the inert protein, retained their activity and specificity. The enzymic yield was found to be 50 percent, using acetyl tyrosyl ethyl ester as a substrate.

The product was dried, either by freeze-drying or simply by air at low temperature. Sterilization was carried out with ultra-violet rays. The product could be preserved in sterile bags.

Equivalent results are obtained by replacing the α-chymotrypsin of this example with any other enzyme having a molecular weight of less than about 200,000.

EXAMPLE 14

Comparative tests were carried out, the results of which are shown in Table I hereinafter.

They consisted of testing various enzymes in order to determine the enzymic yield (1) obtained after reticulation of said enzyme in a carrier and (2) obtained after immobilization with an inactive protein according to this invention.

In the first case, the enzyme preparation was fixed onto various insoluble carriers listed in Table I. For example, when a sheet of aminated paper was used, it was washed with 0.5N NaOH and then water, 0.5N HCl and water until free of chloride. The wet sheet was washed with acetone, dried and then ground. One gram of dry aminated paper powder was added to 0.5 g of enzyme dissolved in 10 ml of water; then 0.4 ml of 50 percent glutaraldehyde was added, and the suspension was adjusted to the required pH.

The solution was stirred at room temperature.

After reaction, the suspension was centrifuged, and the residue was washed several times with 0.1M sodium carbonate, water, 0.01N HCl, water until neutral, and was then freeze-dried.

In the second case, the coreticulation was conducted according to the process of this invention, as described in either Example 5 or Example 8, the inactive protein being indicated in parentheses in Table I.

TABLE I

| | Enzymes Efficiently Bound | |
|---|---|---|
| Bound Enzymes | Yield obtained by immobilization in a Carrier | Yield obtained by co-crosslinking with an inactive protein |
| Oxido Reductases | | |
| glucose oxidase | 10% on Cellophane | 80% (albumin) |
| urate oxidase | 5% on Cellophane | 30% (albumin) |
| L-amino-acid oxidase | | 50% (albumin) |
| xanthine oxidase | | 60% (albumin) |
| catalase | 5% on activated carbon | 80% (albumin) |
| peroxidase | 5% on Whatman 3 paper | 60% (albumin) |
| Transferases | | |
| hexokinase | 3% on aminated paper | 30% (albumin) |
| ribonuclease | | 30% (albumin) |
| Isomerases | | |
| glucose-6 phosphate isomerase | | 50% (hemoglobin) |
| triose-phosphate isomerase | | |
| Lyases | | |
| carbonic anhydrase | 5% on silicone sheet | |
| tyrosine decarboxylase | | 50% (albumin) |
| phenylalanine decarboxylase | | 60% (albumin) |
| Hydrolases (some examples) | | |
| α-amylase | 2% on silk | 80% (albumin) |
| β-galactosidase | nil (Cellophane) | |
| trypsin | 30% on Cellophane | |
| chymotrypsin | 30% on Cellophane | |
| urease | nil | 60% (albumin) |
| asparaginase | | 30% (albumin) |

As it clearly appears from the above table, the process according to this invention always gives unpredictably better results.

EXAMPLE 15

Further Comparative Tests

I. 500 mg. portions of trypsin were separately dissolved in 10 ml of each of the following buffers:
 (A) 0.1M acetate buffer (pH 5.0)
 (B) 0.1M phosphate buffer (pH 6.0)
 (C) 0.1M phosphate buffer (pH 7.0)
 (D) 0.1M phosphate buffer (pH 8.0) before adding 0.4 ml of 50 percent (aq) glutaraldehyde thereto.

At pH 5.0 and pH 6.0 an insoluble colloidal precipitate with no mechanical strength formed after from two to three hours, At pH 7.0 and pH 8.0 no insoluble product was obtained even after 24 hours. A colloidal-type precipitate is obtained by adding ammonium sulfate, but this precipitate is the same as that which is similarly obtained by adding ammonium sulfate to the native enzyme (trypsin) without any glutaraldehyde.

These results confirm the need for inactive protein.

II. Each of (A), (B), (C) and (D) was repeated six times, each time adding a different amount (according to the following schedule) of Bovine Serum Albumin (BSA) to the buffered trypsin prior to admixing the glutaraldehyde therewith:
  (a) 100 mg of BSA
  (b) 200 mg of BSA
  (c) 300 mg of BSA
  (d) 400 mg of BSA
  (e) 500 mg of BSA
  (f) 600 mg of BSA A precipitate appeared in each of (a) through (e). The mechanical properties of the precipitates improved with increased concentration of BSA. With over 50 percent of BSA (based on total protein) the solution (f) set to a mass in the beaker before any precipitation. None of the obtained products (a) through (e) had mechanical properties (physical strength) adequate for any practical application, for example, in an open reaction vessel. These products could not, in any known way, be formed into a self-supporting sheet or membrane.

III. (a) Example 2 was repeated with the glutaraldehyde being replaced by an equivalent amount of carbodiimide, and solvent was similarly permitted to evaporate while the solution was spread on the flat-bottomed glass mold. No solid shaped product materialized.

III. (b) Example 2 was repeated with the glutaraldehyde being replaced by an equivalent amount of bis-diazo-o-anisidine, and solvent was similarly permitted to evaporate while the solution was spread on the flat-bottomed glass mold. No solid shaped product materialized.

III. (c) 25 mg of glucose-oxidase were dissolved in 0.7 ml of phosphate buffer at pH 6.8, and 50 mg of albumin were dissolved in 0.7 ml of the same buffer. The two solutions were mixed and agitated until a homogeneous admixture was obtained. Cold carbo-diimide was added to a concentration of 3 percent. The solution was immediately frozen at −60° C. After 2 hours, the product was slowly thawed. No insoluble phase resulted.

III. (d) Procedure III. (c) was repeated with replacement of the carbo-diimide by the same amount of bis-diazo-o-anisidine. No insoluble phase resulted.

These results establish the lack of equivalency of different water-soluble bi- or polyfunctional crosslinking agents.

IV. (a) Repeating the procedures of Examples 2 to 4, 6, 8 and 10 to 13 with replacement of glutaraldehyde (having 5 carbon atoms) by an equivalent of butyraldehyde (having 4 carbon atoms) and with replacement of the active protein of Examples 3, 4, 6, 8 and 11 to 13 by a corresponding amount of glucose-oxidase results in neither a shaped product resembling a self-sustaining membrane nor a porous sponge-like structure; the glucose-oxidase remains soluble and partially denatured.

IV. (b) Repeating the procedures of Examples 2 to 4, 6, 8 and 10 to 13 with replacement of glutaraldehyde (having 5 carbon atoms) by an equivalent of caproic dialdehyde (having 6 carbon atoms) and with replacement of the active protein of Examples 3, 4, 6, 8 and 11 to 13 by a corresponding amount of glucose-oxidase results in neither a shaped product resembling a self-sustaining membrane nor a porous sponge-like structure; the glucose-oxidase remains soluble and partially denatured.

IV. (c) Repeating the procedures of Examples 2 to 4, 6, 8 and 10 to 13 with replacement of glutaraldehyde (having 5 carbon atoms) by an equivalent of butyraldehyde (having 4 carbon atoms) and with replacement of the active protein by a corresponding amount of $\beta$-glucosidase results in neither a shaped product resembling a self-sustaining membrane nor a porous sponge-like structure; the $\beta$-glucosidase remains soluble and partially denatured.

IV. (d) Repeating the procedures of Examples 2 to 4, 6, 8 and 10 to 13 with replacement of glutaraldehyde (having 5 carbon atoms) by an equivalent of caproic dialdehyde and with replacement of the active protein by a corresponding amount of $\beta$-glucosidase results in neither a shaped product resembling a self-sustaining membrane nor a porous sponge-like structure; the $\beta$-glucosidase remains soluble and partially denatured.

These results establish that replacing glutaraldehyde with an aldehyde having one less carbon atom or a dialdehyde having one more carbon atom yields significantly different products.

The invention and its advantages are readily understood from the preceding description. Various changes may be made in the processes and in the products without departing from the spirit or scope of the invention or sacrificing its material advantages. Exemplified products and processes are merely illustrative of preferred embodiments.

What is claimed is:

1. A product which consists essentially of immobilized active protein in the form of a compound in which the active protein is homogeneously distributed and correlated with and thus chemically bound to inactive protein through glutaraldehyde-based bridges, the weight ratio of active protein to inactive protein in the compound being at most 1 to 4 and the proportion of glutarladehyde bridges in said compound being sufficient to immobilize the active protein.

2. A product according to claim 1 wherein the active protein is a member selected from the group consisting of antigen, allergen, antibody, hormone, enzyme and proteinic part of a virus or of a cell.

3. A product according to claim 1 wherein the active protein is a member selected from the group consisting of oxidase, hydroxylase, isomerase, transferase, lyase and oxidoreductase.

4. A product according to claim 1 wherein the active protein is a member selected from the group consisting of pepsin, subtilisin, trypsin, chymotrypsin and papain.

5. A product according to claim 1 wherein the active protein is a member selected from the group consisting of glucose-oxidase, carbonic anhydrase, lipolytic hydrolase, amylolytic hydrolase, urease, asparaginase, uricase, peroxidase, catalase, phenylalanine-hydroxylase, galactose phosphate uridyl transferase, pronase, collagenase, keratinase, elastase, urate oxidase, tyrosine decarboxylase, hexokinase, phosphatase, L-amino-acid-oxidase, xanthine oxidase, decarboxylase, ribonuclease, $\alpha$-amylase and $\beta$-galactosidase.

6. A product according to claim 1 wherein the active protein substantially retains both its activity and specificity.

7. A shaped solid product having useful mechanical strength and consisting essentially of immobilized active protein according to claim 1.

8. A product according to claim 1 wherein the inactive protein is a member selected from the group consisting of albumin, plasma protein, ovalbumin, fibrinogen, gelatin and hemoglobin.

9. A product according to claim 1 wherein the inactive protein is that found in microbes.

10. A product according to claim 1 wherein the inactive protein is albumin.

11. A product according to claim 2 wherein the inactive protein is a member selected from the group consisting of albumin, plasma protein, ovalbumin, fibrinogen, gelatin, hemoglobin and inactive protein found in microbes.

12. A product according to claim 3 wherein the inactive protein is a member selected from the group consisting of albumin, plasma protein, ovalbumin, fibrinogen, gelatin, hemoglobin and inactive protein found in microbes.

13. A product according to claim 4 wherein the inactive protein is a member selected from the group consisting of albumin, plasma protein, ovalbumin, fibrinogen, gelatin, hemoglobin and inactive protein found in microbes.

14. A product according to claim 5 wherein the inactive protein is a member selected from the group consisting of albumin, plasma protein, ovalbumin, fibrinogen, gelatin, hemoglobin and inactive protein found in microbes.

15. A product according to claim 7 wherein the inactive protein is a member selected from the group consisting of albumin, plasma protein, ovalbumin, fibrinogen, gelatin, hemoglobin and inactive protein found in microbes.

16. A product according to claim 1 wherein the inactive protein is gelatin.

17. A product according to claim 1 wherein the active protein is an antigen.

18. A product according to claim 1 wherein the active protein is an antibody.

19. A product according to claim 1 wherein the active protein is an allergen.

20. A product according to claim 1 wherein the active protein is a part of a virus.

21. A product according to claim 6 wherein the inactive protein is that of a microbe.

22. A product according to claim 1 wherein the active protein and the inactive protein are derived from a single impure source.

23. A product according to claim 22 wherein the single impure source is a microbe source.

24. A self-sustaining flexible sheet or film of immobilized active protein according to claim 1 which is free from a separate or distinct carrier.

25. A sheet or film of immobilized active protein according to claim 1 in combination and integral with an inert non-proteinic carrier which imparts form and strength thereto.

26. A sheet or film according to claim 25 wherein the immobilized active protein is diffused throughout the carrier, which is macroporgus.

27. A sheet or film of immobilized active protein according to claim 25 wherein the carrier is of a material selected from the group consisting of cellulose, regenerated cellulose, amylose, an alginate, a polysilane, polyvinyl alcohol, aminated paper, a polyacrylamide, silicone sheet, activated carbon and silk.

28. Open-cell foam or sponge which consists essentially of immobilized active protein according to claim 1.

29. A product according to claim 1 wherein the active protein is hydrolytic enzyme.

30. A product according to claim 1 wherein the active protein is proteolytic hydrolase.

31. A product according to claim 2 wherein the active protein substantially retains both its activity and specificity, and the inactive protein is a member selected from the group consisting of albumin, plasma protein, ovalbumin, fibrinogen, gelatin and hemoglobin.

32. A product according to claim 1 which, when free from a separate or distinct carrier, is capable of being in a shaped self-supporting form selected from the group consisting of flexible sheet, flexible film, open-cell foam and sponge.

33. A product according to claim 32 which is free from a separate or distinct carrier.

34. A product according to claim 33 which is in one of the stated shaped self-supporting forms.

35. A product according to claim 1 which consists essentially of self-supporting solid.

* * * * *